US007087233B2

(12) United States Patent  (10) Patent No.: US 7,087,233 B2
Chung et al.  (45) Date of Patent: Aug. 8, 2006

(54) ANTIMUTAGENIC EFFECTS OF GANODERMA LUCIDUM SPORES

(75) Inventors: Chee-Keung Chung, Room 2018, Argyle Centre, 688 Nathan Road, Mongkok, Kowloon (HK); Siu Kan Tong, Kowloon (HK)

(73) Assignee: Chee-Keung Chung, Kowloon (HK)

( * ) Notice: Subject to any disclaimer, the term of this patent is extended or adjusted under 35 U.S.C. 154(b) by 0 days.

(21) Appl. No.: 10/189,240

(22) Filed: Jul. 5, 2002

(65) Prior Publication Data

US 2004/0009189 A1  Jan. 15, 2004

(51) Int. Cl.
   *A61K 36/04*  (2006.01)
(52) U.S. Cl. ............................. 424/195.15; 435/254.1
(58) Field of Classification Search ........... 424/195.15; 435/254.1
   See application file for complete search history.

(56) References Cited

U.S. PATENT DOCUMENTS

| | | | |
|---|---|---|---|
| 4,472,907 A | | 9/1984 | Wada et al. |
| 5,595,756 A | * | 1/1997 | Bally et al. ................. 424/450 |
| 6,210,950 B1 | | 4/2001 | Johnson et al. |
| 6,316,002 B1 | * | 11/2001 | Liu et al. ............... 424/195.15 |

FOREIGN PATENT DOCUMENTS

| | | |
|---|---|---|
| EP | 1092765 A2 | 4/2001 |
| EP | 1245235 A2 | 10/2002 |

OTHER PUBLICATIONS

Gura, T. Systems for Identifying New Drugs are Often Faulty; Science, Nov. 7, 1997, vol. 278, pp. 1041-1042.*
Lee, Seung Y.; Cardiovascular Effects of Mycelium Extract of *Ganoderma lucidum*: Inhibition of Sympathetic Outflow as a Mechanism of Its Hypotensive Action. Chem Pharm. Bull. vol. 38, p. 1359-1364 (1990).
Kim et al., Int. J. Mol. Med vol. 4(3), p. 273-277 (1999).
Lin et al . J. Ethnopharmacol., vol. 47(1), p. 33-41 (1995).
El Mekkawy, Sahar et al., Anti-HIV-1 and Anti-HIV-A-Protease Substances from *Ganoderma lucidum* Phytpchemistry, vol. 49(6), p. 1651-1657 (1998).
Wasser, Solomon P., et al., Therapeutic Effects of Substances Occurring in Higher Basidiomycetes Mushrooms: A Modern Perspective; Crit. Rev. Immunol., vol. 19(1), p. 65-96 (1999).
Miyazaki, Toshio et al., Studies on Fungal Polysac-charidesXXVII, Structural Examination of a Water-soluble. Antitumor Polysaccharide of *Ganoderma lucidum*; Chem. Pharm. Bull., vol. 29(12), p. 3611-3616 (1981).
Min, Byung-Sun et al., Triterpenes from the Spores of *Ganoderma lucidum* and Their Inhibitory Activity against HIV-1 Protease. Chem. Pharm. Bull., vol. 46(10), p. 1607-1612 (1998).

Kino, K. et al., An immunomodulating protein, LING ZHI-8(LZ-8) prevents insulitis an non-obese diabetic mice, Diabetologia, vol. 33, p. 713-718 (1990).
Vander Hem et al., LING ZHI-8: Studies of a New Immunomodulating Agent, Transplantation, vol. 60, p. 438-443 (1995).
Kino, Kohsuke et al., Immunomodulator, LZ-8, Prevents Antibody Production in Mice; Int. J. Immunopharmac., vol. 13(8), p. 1109-1115 (1991).
Maruyama, Hirofumi; Antitumor Activity of Sarcodon aspratus (BERK) S. IIO and *Ganoderma lucidum* (FR.) KARST., J. Pharmacobio-Dyn,m vol. 12, p. 118-123 (1989).
Shimizu, Akira et al.; Isolation of an Inhibitor of Platelet Aggregation from a Fungus, *Ganoderma lucidum*; Chem. Pharm. Bull., vol. 33, p. 3012-3015 (1985).
Morigiwa, Aiko et al.; Angiotension Converting Enzyme-Inhibitory Triterpenes from *Ganoderma lucidum*; Chem. Pharm. Bull., vol. 34(7), p. 3025-3028 (1986).
Kanmatsuse, Katsuo et al.; Studies on *Ganoderma lucidum*. I. Efficacy against Hypertension and Side Effects; Yakugaku Zasshi, vol. 105(10), p. 942-947 (1985).
Lieu, Chien-Whei et al.; The Effect of *Ganoderma lucidum* on Induction of Differentiation in Leukemic U937 Cells; Anticancer Research, vol. 12, p. 1211-1216 (1992).
Wang, Sheng-Yuan et al.; The Anti-Tumor Effect of *Ganoderma lucidum* is Mediated by Cytokines Released From Acticviated Macrophages and T Lymphocytes; Int. J. Cancer, vol. 70, p. 699-705 (1997).
O'Neil, Carol E. et al.; Basidiospere Extracts: Evidence for Common Antigenic/Allergenic Determinants; Int. Archs Allergy appl. Immun., vol. 85, p. 161-166 (1988).
Nogami, Mari et al.; Studies on *Ganoderma lucidum*VI. Anti-allergic Effect. (1); Yakugaku Zasshi, vol. 106(7), p. 594-599 (1986), English Abstract.
Gengtao et al.; Some Pharamacological Actions of the Spores of *Ganoderma lucidum* and the Mycelium of Ganoderma Capense (Lloyd)Teng Cultivated by Submerged Fermentation; Chinese Medical Journal, vol. 92(7), p. 496-500 (1979).
Fu, Huidi et al.; The Clinical Effects of *Ganoderma lucidum* Spore Preparations in 10 Cases of Atrophic Myotonia: Journal of traditional Chinese Medicine, vol. 2(1), p. 63-65 (1982).

(Continued)

*Primary Examiner*—Patricia Leith
(74) *Attorney, Agent, or Firm*—Fei-Fei Chao; Bingham McCutchen LLP

(57) ABSTRACT

The present invention provides a method for fetal protection by orally administering germination activated *Ganoderma lucidum* spore powder ("GASP") to pregnant mammals. GASP demonstrates prophylactic effects on fetal damage in pregnant mammals, particularly humans.

7 Claims, No Drawings

OTHER PUBLICATIONS

Mizushina, Yoshiyuki et al.; A Mushroom Fruiting Body-Inducing Substance Inhibits Activities of Replicative DNA Polymerases; *Biochemical and Biophysical Research Communications*, vol. 249, p. 17-22 (1998).

Lin, Lee-Juian et al.; Separation of oxygenated triterpenoids from *Ganoderma lucidum* by high-performance liquid chromatography; *Journal of Chromatography*, vol. 410, p. 195-200 (1987).

Kino, Kohsuke et al.; Isolation and Characterization of a New.

*Ganoderma lucidum* and Panax gingseng inhibit aflatoxin B1 and benzo(a)pyrene-induced mutagenesis in *Salmonella typhimurium* TA98 and TA100. B.Y.Y Wong & H.H.L. Wong, Abstracts of the General Meeting of the American Society for Microbiology, (2001), 101, 406-407. (See abstract).

Effect of mycelial culture broth of *Ganoderma lucidum* of the growth characteristics of human cell lines, W.T Chung et al, Journal of Bioscience and Bioengineering, (2001), 92. 550-555. (See abstract).

WPI Abstract Accession No. 2001-503343/56 & CN 1298741, (University of Zhongshan) (See abstract).

* cited by examiner

ANTIMUTAGENIC EFFECTS OF *GANODERMA LUCIDUM* SPORES

BACKGROUND OF THE INVENTION

1. Field of the Invention

This invention relates to the use of germination activated *Ganoderma lucidum* spore powder for fetal protection. Specifically, the invention relates to a method for preventing fetal damage by the administration of germination activated *Ganoderma lucidum* spore powder to a pregnant mammal.

2. Background Information

Germination activated *Ganoderma lucidum* spore powder (GASP) is a brown powder, slightly soluble in water, and is useful for a wide variety of medicinal and health purposes. Means for production of GASP are described in U.S. Pat. No. 6,316,002 B1, which is herein incorporated by reference. It is available commercially from Guangzhou Green Food Project Company of the College of Life Sciences, Zhongshan University and Green Power Health Products International Co. Ltd., Sweden and Hong Kong.

GASP has been used, or proposed for use, in immunological disorders, hepatis, AIDS, cancer, diabetes, preventing free radical oxidation, inhibiting hepatotoxic activity, and for treating cardiovascular diseases, bacterial or viral infections, inter alia. To date, however, there have been no reports on the effects of GASP during pregnancy or on the developing fetus.

SUMMARY OF THE INVENTION

The present inventors have unexpectedly found that GASP, when administered to a pregnant mammal, exhibits a protective effect on the fetus. This protective effect is an antimutagenic/antiteratogenic effect that reduces or eliminates chromosomal aberations that may be caused by cyclophosphamide (CP) and analogous harmful substances that may be found in the environment.

It is therefore an object of the invention to provide a method of protecting a fetus comprising administering an effective protective amount of GASP to a pregnant mammal. In a preferred embodiment, GASP is administered to a pregnant human.

However, the method will be effective in mammals generally, including rats, mice, dogs, cats, rabbits, cattle, sheep, etc., including higher nonhuman primates. In particular, it is an object of the invention to provide a method of protecting a fetus from mutations, including chromosomal aberrations, that may be caused by toxic substances in the environment, or by ultraviolet or ionizing radiation.

By "teratogenic" is meant having the property of increasing the incidence of congenital or developmental malformations. A teratogen may be a chemical compound, a genetic locus of the fetus or the pregnant female (see e, U.S. Pat. No. 6,210,950, which is incorporated herein by reference), or a physical force in the environment, such as ultraviolet or ionizing radiation, electromagnetic radiation, and the like.

Although the exact mechanism of action of GASP is unknown, it is proven by the inventors of the present invention that administration of GASP to a pregnant female mammal reduces the incidence of developmental malformations, fetal death, and birth defects caused by any sources.

By "mutagenic" is meant causing a structural change in a chromosome or gene.

It is one object of the invention to provide a method for protecting a fetus from mutagenic compounds to which a pregnant female may be exposed, and for protecting the fetus from the teratogenic effects of such compounds. Examples of such mutagenic compounds include, but are not limited to, cyclophosphamide, arsenic, Aflatoxin $B_1$, vinyl chloride, acetylamino fluorene, Safrole, dimethylnitrosamine, benzo(a)pyrine, dibenzanthracene, nitrogen mustard, β-propiolactone, ethylmethane sulfonate, methyl nitrosourea and dimethyl sulfate. Numerous mutagenic compounds are familiar to those of skill in the art, and can be identified by tests known to those of skill in the art. While pregnant mammals, particularly humans, are not normally deliberately exposed to such compounds, small amounts of these and other compounds that may affect the fetus may be present in the environment.

It is another object of the invention to provide a means of reducing developmental and birth defects in a mammal, particularly a human.

These and other objects of the invention are accomplished by the administration of GASP to a pregnant female mammal, particularly a human.

In humans, GASP is preferably administered in a dosage amount between 0.5 g/day and 50 g/day per person, more preferably between 1 and 25 g/day per person, with the usual recommended dose being 4.8 g/day. It is believed that for optimum benefit, GASP should be used throughout pregnancy.

For administration to other mammals, such as for veterinary purposes, the effective dosage is expected to be roughly equivalent in terms of the amount administered per body mass of the recipient animal, and can be determined through routine experimentation by persons of skill in the art.

Administration of GASP according to the methods of the invention prevents or reduces the incidence or likelihood of fetal death, mutagenic damage, and developmental or birth defects in the fetus.

DETAILED DESCRIPTION OF THE INVENTION

In describing preferred embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLE 1

In order to demonstrate that GASP had antimutagenic activity, a mouse model was employed to show that multiple administration of GASP could inhibit the mice bone marrow cell chromosomal aberration induced by cyclophosphamide ("CP").

The test used was the modified mice bone marrow cell micronucleus test as specified in "A Notice Concerning Issuance of the Revised Items of the 'Health Food Functional Assessment Procedures and Testing Methods'," a document from the Ministry of Public Health of the People's Republic of China, which is hereby incorporated by reference.

Germination activated *Ganoderma lucidum* spore powder Batch No. 2000118 was obtained from Guangzhou Green Food Project Company of the College of Life Sciences, Zhongshan University and Green Power Health Products International Co. Ltd., Sweden and Hong Kong.

Ninety (90) NIH mice, half males and half females, weighing 18–20 g were obtained from Guangdong Provincial Animal Center for Medical Experiments, Certificate of Conformity Number: 200A025.

The recommended clinical dosage of GASP was 4.8 g/day/person, which was converted according to the respective body mass of humans and mice. This was equivalent to a dosage in mice of 0.61 g/kg, (4.8 g÷7.9=0.61 g/kg). About 10 times of the recommended clinical dosage of GASP did not appear to cause adverse effects in humans and mice. If the high dosage group was given 10 times of the daily dose, then, the three mice dosage groups were respectively given 6.10 g/kg, 3.10 g/kg, and 0.61 g/kg, which were equivalent to 10, 5, and 1 times the clinical dosage in humans.

The mice were randomly divided by weight into 9 groups, 5 males and 5 females respectively per group. Animals in each group were given the following treatment:

Group 1 received 6.1 g/kg of GASP and 50 mg/kg of cyclophosphamide ("CP").
Group 2 received 3.1 g/kg of GASP and 50 mg/kg of CP.
Group 3 received 0.6 g/kg of GASP and 50 mg/kg of CP.
Group 4 received 0 g/kg of GASP and 50 mg/kg of CP.
Group 5 received 6.1 g/kg of GASP and 40 mg/kg of CP.
Group 6 received 3.1 g/kg of GASP and 40 mg/kg of CP.
Group 7 received 0.6 g/kg of GASP and 40 mg/kg of CP.
Group 8 received 0 g/kg of GASP and 40 mg/kg of CP.
Group 9 received 0 g/kg of GASP and 0 mg/kg of CP.

The males and females in each group were housed in separate cages. The experiment was conducted for a period of 30 days. During this time period, food consumption and abnormal appearance of the animals were closely monitored and the weight variations of the animals were recorded every 3 to 7 days.

The drug was prepared as a suspension of the required concentration in distilled water, and administered orally through tube at individual dosages of 0.2 mL/10 g of body weight. The negative control group was given distilled water of the equivalent volume through tube once a day for 30 days continuously. On the 30th day of the test the subject drug groups and the positive control groups were administered CP orally once at 40 and 50 mg/kg, respectively. One (1) hour after the administration of CP, the subject drug groups and the negative control group were once again given the subject drug and distilled water, and 24 hours after the last administration the mice were sacrificed. 4 hours before the mice were sacrificed they are given colchicine, and the bone marrow was extracted in order to prepare the chromosome samples in the routine way.

Samples from each group were observed. One hundred (100) metaphase cells per mouse were observed, and the chromosomal structures and the numbers of aberrations were recorded. Using SPSS for Windows 8.0 (t-test), a comparative analysis was made of the experimental data from the various dosage groups and the positive groups and tested to find out if there was any significant difference between the males and females within the group.

The weights of the mice in the various groups during the test period of 30 days are shown in Table 1. The data indicate that the weights of the animals of the various test groups and the negative control group show no significant difference ($p>0.05$). The results indicate that the various dosages of GASP have no effects on the weight gain of the mice.

TABLE 1

Variation in the Weight of the Mice During the Period of Administration of the Germination Activated *Ganoderma lucidum* Spore Powder ($\bar{X} \pm S$, g)

| Group | Dosage of test drug (g/kg) | CP dosage (mg/kg) | Number of animals | Gender | Day 0 | Day 4 | Day 8 | Day 15 | Day 22 | Day 29 | Net weight gain |
|---|---|---|---|---|---|---|---|---|---|---|---|
| 1 | 6.1 | 50 | 5 | M | 20.5 ± 0.7 | 20.0 ± 1.8 | 25.0 ± 1.4 | 25.0 ± 2.9 | 26.3 ± 2.6 | 28.1 ± 3.1 | 7.6 ± 2.8 |
|   | 6.1 | 50 | 5 | F | 18.1 ± 0.1 | 19.9 ± 1.3 | 22.3 ± 1.7 | 22.5 ± 1.7 | 23.6 ± 1.2 | 25.5 ± 1.0 | 7.4 ± 1.0 |
| 2 | 3.1 | 50 | 5 | M | 20.2 ± 1.2 | 22.1 ± 1.3 | 24.2 ± 1.7 | 26.2 ± 2.6 | 29.6 ± 3.8 | 31.0 ± 3.6 | 10.8 ± 4.1 |
|   | 3.1 | 50 | 5 | F | 18.4 ± 0.5 | 19.9 ± 1.1 | 22.3 ± 1.5 | 23.6 ± 2.3 | 24.7 ± 2.0 | 26.2 ± 1.2 | 7.8 ± 1.1 |
| 3 | 0.6 | 50 | 5 | M | 18.7 ± 1.6 | 21.1 ± 0.5 | 24.1 ± 2.7 | 26.1 ± 3.3 | 28.9 ± 3.0 | 29.6 ± 2.5 | 10.4 ± 3.4 |
|   | 0.6 | 50 | 5 | F | 18.3 ± 0.4 | 19.3 ± 0.9 | 20.9 ± 1.3 | 22.0 ± 0.5 | 22.9 ± 0.7 | 25.2 ± 0.4 | 6.9 ± 0.5 |
| 4 | 0 | 50 | 5 | M | 19.8 ± 1.5 | 21.0 ± 1.7 | 24.8 ± 3.2 | 25.1 ± 4.6 | 26.3 ± 1.6 | 27.9 ± 1.6 | 8.1 ± 1.8 |
|   | 0 | 50 | 5 | F | 18.2 ± 0.4 | 19.3 ± 2.0 | 21.8 ± 1.9 | 23.2 ± 1.8 | 24.3 ± 2.1 | 25.9 ± 1.0 | 7.6 ± 0.9 |
| 5 | 6.1 | 40 | 5 | M | 19.4 ± 1.2 | 21.8 ± 1.1 | 24.4 ± 0.5 | 24.5 ± 2.1 | 28.2 ± 3.1 | 28.9 ± 2.2 | 8.8 ± 2.9 |
|   | 6.1 | 40 | 5 | F | 18.1 ± 0.9 | 19.8 ± 1.8 | 21.9 ± 2.1 | 23.6 ± 2.1 | 24.6 ± 2.4 | 25.9 ± 1.3 | 7.9 ± 1.3 |
| 6 | 3.1 | 40 | 5 | M | 20.5 ± 1.0 | 21.3 ± 1.3 | 23.3 ± 3.4 | 25.4 ± 3.2 | 27.5 ± 2.8 | 29.3 ± 3.0 | 8.7 ± 2.4 |
|   | 3.1 | 40 | 5 | F | 18.4 ± 0.3 | 19.7 ± 0.8 | 20.9 ± 0.9 | 22.2 ± 0.8 | 23.7 ± 1.4 | 25.7 ± 1.6 | 7.2 ± 1.8 |
| 7 | 0.6 | 40 | 5 | M | 20.3 ± 1.0 | 23.0 ± 1.2 | 25.7 ± 1.2 | 27.7 ± 1.9 | 31.3 ± 3.3 | 33.2 ± 3.8 | 12.8 ± 3.9 |
|   | 0.6 | 40 | 5 | F | 18.3 ± 0.3 | 21.1 ± 0.7 | 23.6 ± 0.6 | 25.0 ± 0.4 | 26.8 ± 1.4 | 26.8 ± 0.4 | 8.4 ± 0.4 |
| 8 | 0 | 40 | 5 | M | 19.4 ± 1.3 | 22.8 ± 1.3 | 26.0 ± 1.3 | 28.1 ± 1.3 | 32.4 ± 1.8 | 33.2 ± 2.0 | 13.7 ± 1.8 |
|   | 0 | 40 | 5 | F | 18.2 ± 0.2 | 19.6 ± 1.2 | 22.9 ± 1.0 | 24.8 ± 0.6 | 27.1 ± 2.3 | 27.5 ± 2.1 | 9.3 ± 1.8 |
| 9 | 0 | 0 | 5 | M | 19.7 ± 1.3 | 22.8 ± 0.9 | 25.4 ± 1.1 | 26.6 ± 1.4 | 29.0 ± 3.8 | 30.1 ± 3.6 | 10.4 ± 4.5 |
|   | 0 | 0 | 5 | F | 18.0 ± 0.2 | 20.6 ± 0.5 | 22.8 ± 0.4 | 24.2 ± 1.5 | 25.7 ± 0.5 | 26.3 ± 1.0 | 8.3 ± 1.0 |

The rate of bone marrow cell chromosomal aberration induced by 50 mg/kg CP in the various dosage groups of GASP (Groups 1, 2, and 3) was noticeably lower than the positive control group, as shown in Table 2. The difference between the various dosage groups and the positive control group was significant ($p<0.01$). The inhibition rate of the GASP on the mice chromosomal aberration induced by CP was over 50% on the average. The results also demonstrate that there was a dose-dependent relationship between the increase in the dose of GASP and the increased inhibitory effect on chromosomal aberration.

TABLE 2

Inhibitory Effect of the Germination Activated *Ganoderma lucidum* Spore Powder on the Mice Bone Marrow Cell Chromosomal Aberrations Induced by 50 mg/kg of CP

| | GROUP | | | | | | | | | |
|---|---|---|---|---|---|---|---|---|---|---|
| | 1 | 1 | 2 | 2 | 3 | 3 | 4 | 4 | 9 | 9 |
| GASP Tested Dosage (g/kg) | 6.1 | 6.1 | 3.1 | 3.1 | 0.61 | 0.61 | 0 | 0 | 0 | 0 |
| CP Dosage (mg/kg) | 50 | 50 | 50 | 50 | 50 | 50 | 50 | 50 | 0 | 0 |
| No. of Animals | 5 | 5 | 5 | 5 | 5 | 5 | 5 | 5 | 5 | 5 |
| Gender | M | F | M | F | M | F | M | F | M | F |
| No. Cells Counted | 500 | 500 | 500 | 500 | 500 | 500 | 500 | 500 | 500 | 500 |
| Abberant Cell Count | 64 | 71 | 78 | 90 | 103 | 98 | 198 | 221 | 9 | 7 |
| No. of Abnormalities Polyploid | 2 | 2 | 4 | 3 | 3 | 2 | 9 | 5 | 1 | 2 |
| No. of Abnormalities hyperploid | 1 | 2 | 1 | 2 | 1 | 1 | 2 | 5 | 0 | 0 |
| No. of Abormal Cells | 3 | 4 | 5 | 5 | 4 | 3 | 11 | 10 | 1 | 2 |
| Abnormality Rate | 0.6 | 0.8 | 1.0 | 1.0 | 0.8 | 0.6 | 2.2 | 2.0 | 0.2 | 0.4 |
| ctg[1] | 9 | 9 | 5 | 13 | 9 | 11 | 18 | 18 | 0 | 0 |
| csg[2] | 0 | 0 | 0 | 0 | 0 | 0 | 0 | 0 | 0 | 0 |
| crb[3] | 51 | 62 | 68 | 77 | 90 | 89 | 170 | 185 | 9 | 7 |
| csb[4] | 11 | 7 | 9 | 11 | 16 | 14 | 33 | 21 | 0 | 0 |
| f[5] | 22 | 23 | 26 | 30 | 37 | 36 | 100 | 117 | 0 | 0 |
| tr[6] | 3 | 2 | 4 | 7 | 9 | 5 | 29 | 32 | 0 | 0 |
| dmin[7] | 0 | 0 | 0 | 0 | 0 | 0 | 0 | 0 | 0 | 0 |
| del[8] | 17 | 18 | 22 | 26 | 35 | 31 | 92 | 103 | 0 | 0 |
| r[9] | 0 | 0 | 0 | 0 | 0 | 0 | 1 | 0 | 0 | 0 |
| Cell Aberration Rate (%) | 12.8* | 14.2 | *15.6 | *18.0 | *20.6 | *19.6 | *39.6 | 44.2 | 1.8 | 1.4 |
| Inhibition Rate (%) | 67.6 | 67.8 | 60.6 | 59.3 | 50.5 | 55.6 | — | — | — | — |

[1] ctg: chromatid gap.
[2] csg: chromosome gap.
[3] ctb: chromatid break.
[4] csb: chromosome break.
[5] f: fragment.
[6] tr: triradial.
[7] r: ring chromosome
[8] dmin: dimicrobody
[9] del: nullisomic inhibition rate = (cell aberration rate of the positive group – cell aberration rate of the GASP group)/cell aberration rate of the positive group
*p < 0.05 compared with the positive group.
**p < 0.013 compared with the positive group.

As shown in Table 3, the aberration rate (%) of the bone marrow cell chromosomes induced by 40 mg/kg of CP in the various dosage groups (i.e., treated with GASP) was noticeably lower than that of the positive control groups. The difference between the various dosage groups and the positive control group was significant (p21 0.05). The inhibition rate (%) of the various GASP dosage groups on the mice chromosomal aberrations induced by CP was over 30%, however, there was no apparent dose-effect relationship. The results indicate that the GASP has an inhibitory effect on the mice bone marrow cell chromosomal damage induced by CP.

TABLE 3

Inhibitory Effect on the Germination Activated *Ganoderma lucidum* Spore Powder on the Mice Bone Marrow Cell Chromosomal Aberrations Induced by 40 mg/kg of CP

| | GROUP | | | | | | | | | |
|---|---|---|---|---|---|---|---|---|---|---|
| | 5 | 5 | 6 | 6 | 7 | 7 | 8 | 8 | 9 | 9 |
| GASP Tested Dosage (g/kg) | 6.1 | 6.1 | 3.1 | 3.1 | 0.61 | 0.61 | 0 | 0 | 0 | 0 |

TABLE 3-continued

Inhibitory Effect on the Germination Activated *Ganoderma lucidum* Spore Powder on the Mice Bone Marrow Cell Chromosomal Aberrations Induced by 40 mg/kg of CP

| | GROUP | | | | | | | | | |
|---|---|---|---|---|---|---|---|---|---|---|
| | 5 | 5 | 6 | 6 | 7 | 7 | 8 | 8 | 9 | 9 |
| CP Dosage (mg/kg) | 40 | 40 | 40 | 40 | 40 | 40 | 40 | 40 | 0 | 0 |
| No. of Animals | 5 | 5 | 5 | 5 | 5 | 5 | 5 | 5 | 5 | 5 |
| Gender | M | F | M | F | M | F | M | F | M | F |
| No. Cells Counted | 500 | 500 | 500 | 500 | 500 | 500 | 500 | 500 | 500 | 500 |
| Abberant Cell Count | 51 | 48 | 75 | 71 | 48 | 68 | 108 | 118 | 9 | 7 |
| No. of Abnormalities Polyploid | 1 | 2 | 2 | 1 | 2 | 1 | 6 | 5 | 1 | 2 |
| No. of Abnormalities hyperploid | 0 | 1 | 0 | 1 | 0 | 1 | 1 | 1 | 0 | 0 |
| No. of Aborrmal Cells | 1 | 3 | 2 | 2 | 1 | 2 | 9 | 6 | 1 | 2 |
| Abnormality Rate | 0.2 | 0.6 | 0.4 | 0.4 | 0.2 | 0.4 | 1.8 | 1.2 | 0.2 | 0.4 |
| ctg[1] | 8 | 7 | 10 | 3 | 8 | 7 | 18 | 16 | 0 | 0 |
| csg[2] | 0 | 0 | 0 | 0 | 0 | 0 | 0 | 0 | 0 | 0 |
| crb[3] | 41 | 40 | 57 | 61 | 43 | 57 | 94 | 95 | 9 | 7 |
| csb[4] | 2 | 2 | 0 | 0 | 0 | 0 | 19 | 28 | 0 | 0 |
| f[5] | 14 | 13 | 21 | 24 | 16 | 21 | 62 | 60 | 0 | 0 |
| tr[6] | 1 | 5 | 1 | 1 | 2 | 0 | 15 | 21 | 0 | 0 |
| dmin[7] | 0 | 0 | 0 | 0 | 0 | 0 | 0 | 0 | 0 | 0 |
| del[8] | 12 | 11 | 22 | 22 | 15 | 17 | 47 | 50 | 0 | 0 |
| r[9] | 0 | 0 | 0 | 0 | 0 | 0 | 0 | 0 | 0 | 0 |
| Cell Aberration Rate % | 10.2** | 9.6** | 15.0* | 14.2* | 9.6** | 13.6** | 21.6 | 23.6 | 1.8 | 1.4 |
| Inhibition Rate (%) | 52.8 | 59.3 | 30.6 | 39.8 | 55.6 | 42.4 | — | — | — | — |

[1] ctg: chromatid gap.
[2] csg: chromosome gap.
[3] ctb: chromatid break.
[4] csb: chromosome break.
[5] f: fragment.
[6] tr: triradial.
[7] r: ring chromosome
[8] dmin: dimicrobody
[9] del: nullisomic inhibition rate = (cell aberration rate of the positive group − cell aberration rate of the GASP group)/cell aberration rate of the positive group.
*$p < 0.05$ compared with the positive group.
**$p < 0.013$ compared with the positive group.

The results show that 30 days after the mice were given 6.1, 3.1, and 0.61 g/Kg (equivalent to 10, 5, and 1 times the recommended clinical dosage) of the GASP, there was an inhibitory effect on the mice bone marrow cell chromosomal aberrations induced by 40 or 50 mg/kg CP, and of them the inhibition rate of the highest dose group (6.1 g/kg) for the mice bone marrow cell chromosomal aberrations induced by 50 mg/kg CP could reach 67.8%. This demonstrates that the GASP has a protective effect on the mice chromosomal damage induced by cyclophosphamide.

EXAMPLE 2

To test the embryotoxicity and teratogenic effects of GASP, a rat model was used. Sprague Dawley (SD) rats were provided by the Guangdong Provincial Animal Center for Medical Experiments (Certificate of Qualification No.: 2000A026). The rats were observed for one week before use, and passed the quarantine.

The rats were fed standard pellet feed as provided by the Guandong Provincial Animal Center for Medical Use. Healthy SD rats weighing between 200–250 g were selected and housed together overnight at a 2:1 ratio of females to males. Beginning on the next day, vaginal smears were examined each morning, and the date when sperm was found was considered day 0 of pregnancy.

The pregnant rats were randomly divided into 5 groups, 18 rats per group. According to acute toxicity test, the LD50 of the SD rats is greater than 21.5 g/kg. The human clinical dose was four capsules per dose (each capsule containing 0.3 g of the GSAP), four times daily. The study was designed so that the low dose group was 428.6 mg/kg, medium dose group was 2143 mg/kg, and the high dose group was 4286 mg/kg (equivalent to 1, 5, and 10 times the human clinical dose, respectively, when calculated according to the respective body surface areas of the rat and human). During the 6–15 days of the pregnancy, the GASP was orally administered to the rats in the dosage groups at a volume of 1.5 ml/100 g through gavage. The positive control group was given aspirin (250 mg/kg) on days 10–12 of the pregnancy, at the volume of 1.0 ml/100 g orally by means of a stomach tube, while the negative control group was given the equivalent amount of distilled water orally through gavage.

All the pregnant rats were weighed once every 3 days, so as to adjust the dosage. On the day 20 of the pregnancy, the animals were sacrificed by dislocating the vertebra, and a cesarean was performed to obtain the fetal rats in order to check various indexes and for statistical analysis.

Effects on the Weight Gain of the Pregnant Rats

The weight gain of the pregnant rats during the 20 day test period is shown in Table 4. The results indicate that the net weight gain of the group of the animals given aspirin is significantly lower than that of the negative control group ($p<0.05$). A statistical comparison of the various dose groups of the GASP with the negative control group revealed that the net weight gain was not significantly different ($p>0.05$), indicating that the dosage of the GASP in the present experiment had no effect on the weight gain of the pregnant rats.

TABLE 4

Effects of the *Ganoderma lucidum* Spore Powder Activated by Germination on the Weight Gain of the Pregnant Rats (g, $\bar{x} \pm s$)

| | GROUP | | | | |
|---|---|---|---|---|---|
| | Negative Control Group | Positive Control Group | Low Dose Group | Medium Dose Group | High Dose Group |
| Day 0 | 232.4 ± 36.3 | 233.5 ± 11.7 | 222.8 ± 29.7 | 214.9 ± 25.8 | 225.2 ± 29.7 |
| Day 3 | 243.9 ± 36.8 | 253.5 ± 26.8 | 237.9 ± 31.4 | 229.9 ± 23.8 | 238.2 ± 31.0 |
| Day 6 | 254.3 ± 37.3 | 252.8 ± 20.3 | 252.7 ± 30.8 | 241.3 ± 22.4 | 249.5 ± 30.3 |
| Day 9 | 264.6 ± 38.2 | 254.7 ± 14.8 | 260.3 ± 31.9 | 249.8 ± 20.6 | 251.5 ± 28.4 |
| Day 12 | 281.3 ± 39.8 | 269.7 ± 33.4 | 279.2 ± 31.1 | 265.2 ± 23.2 | 270.6 ± 29.1 |
| Day 15 | 299.3 ± 38.6 | 274.8 ± 11.5 | 298.3 ± 34.3 | 285.6 ± 25.8 | 288.4 ± 33.3 |
| Day 18 | 317.7 ± 48.5 | 273.3 ± 16.6 | 332.5 ± 38.1 | 310.4 ± 30.9 | 311.5 ± 37.7 |
| Day 20 | 328.1 ± 46.7 | 281.3 ± 16.4 | 341.2 ± 40.3 | 321.4 ± 37.6 | 320 ± 40.3 |
| Net Weight Gain | 95.7 ± 29.3 | 47.8 ± 13.9 | 118.4 ± 24.4 | 106.5 ± 31.2 | 94.9 ± 42.1 |

*$p < 0.05$.

Effects on Early Embryo Development:

Table 5 shows a comparative study by comparing the means of the three GASP dose groups with the negative control group. The results demonstrate no significant difference in fetal survival rate, absorption rate, and fetal death rate per litter ($p>0.05$) between the GASP treated group and the negative control group. This was significantly different from the studies between the aspirin group (the positive control group) and the negative control group, which showed statistically significant difference ($p<0.01$). The results indicate that the GASP did not have any noticeable effects on early embryo development.

TABLE 5

Effects of the *Ganoderma lucidum* Spore Powder on Early Embryo Development

| Group | No. pregnant rats | No. surviving fetus | Mean no. survivors per litter | No. litters with absorptions | No. of litters with dead fetuses | No. fetal resorption | Fetal Absorption Rate (%) | Mean no. corpora lutea | Mean nidification no. |
|---|---|---|---|---|---|---|---|---|---|
| Negative control group | 17 | 176 | 10.4 | 3 | 2 | 7 | 3.83 | 16.3 | 10.8 |
| Aspirin group | 14 | 56 | 4.0* | 10 | 5 | 94** | 62.66** | 13.5* | 10.7 |
| Low dose group | 17 | 174 | 10.2 | 5 | 1 | 6 | 3.33 | 16.2 | 10.6 |
| Medium dose group | 17 | 188 | 11.1 | 5 | 3 | 8 | 4.08 | 16.4 | 11.5 |
| High dose group | 22 | 234 | 10.6 | 3 | 4 | 9 | 3.70 | 16.0 | 11.0 |

*$p < 0.05$ compared with the negative control group.
**$p < 0.01$ compared with the negative control group.

Effects on the Level of Development of Fetal Rats:

Table 6 shows a comparison of the various dose groups of the GASP with the negative control group in various indexes of fetal rats. The results showed no significant difference (p>0.05) between the GASP groups and the negative control group. However, when comparing the aspirin positive control group with the negative control group, a significant difference, with respect to the appearance of the fetal rats, was observed, which had an appearance abnormality rate of 42.9%. The fetal rats of the aspirin positive control group appeared to be small and had short limbs and tails and umbilical hernias, etc.

TABLE 6

Effects of the *Ganoderma lucidum* Spore Powder Activated by Germination on the Level of Development of Fetal Rats ($\bar{x} \pm s$)

| Dose Group | No. pregnant rats | No. surviving fetus | No. appearance abnormalities | Mean body length (cm) | Mean tail length (cm) | Mean body weight (g) | Mean placental weight (g) |
|---|---|---|---|---|---|---|---|
| Negative control group | 17 | 176 | 0 | 3.77 ± 0.12 | 1.32 ± 0.05 | 3.91 ± 0.36 | 0.69 ± 0.10 |
| Aspirin group | 14 | 56 | 24** | 3.11 ± 0.40* | 1.19 ± 0.09* | 2.76 ± 0.47* | 0.45 ± 0.08* |
| Low dose group | 17 | 174 | 0 | 3.79 ± 0.19 | 1.33 ± 0.05 | 3.98 ± 0.38 | 0.64 ± 0.10 |
| Medium dose group | 17 | 188 | 0 | 3.79 ± 0.15 | 1.33 ± 0.06 | 3.81 ± 0.39 | 0.62 ± 0.09 |
| High dose group | 22 | 234 | 0 | 3.79 ± 0.21 | 1.32 ± 0.07 | 3.96 ± 0.50 | 0.65 ± 0.08 |

*p < 0.05 compared with the negative control group.
**p < 0.01 compared with the negative control group.

Effects on the Skeletal Development of the Fetal Rat:

After alizarin red staining, the fetal rats were observed under the microscope, and the results indicated that there was no significant difference between the various GASP dosage groups and the negative control group with regard to skeletal development (p>0.05), while the aspirin positive control group showed deformations such as dysostosis, costal fusion, bicipital ribs, and vertebral deformation. The results indicate that the GASP at the current dosage did not affect the skeletal development of fetal rats. (Results shown in Table 7).

TABLE 7

Effects of the *Ganoderma lucidum* Spore Powder on the Level of Skeletal Development of Fetal rats

| Dosage Group | No. fetal rats examined | No. deformed fetal rats | Parieto-occipital formation incomplete (no.) | Sternal ossification incomplete (no.) | Costal deformation (no.) | Vertebral deformation (no.) | Fontanelle width (mm) |
|---|---|---|---|---|---|---|---|
| Negative control | 136 | 0 | 5 | 17 | 0 | 0 | 0.25 |
| Aspirin group | 39 | 31** | 28** | 39* | 17** | 10** | 0.27 |
| Low dose group | 135 | 0 | 3 | 15 | 0 | 0 | 0.26 |
| Medium dose group | 135 | 0 | 3 | 16 | 0 | 0 | 0.26 |
| High dose group | 178 | 0 | 1 | 15 | 0 | 0 | 0.25 |

*p < 0.05 compared with the negative control group.
**p < 0.01 compared with the negative control group.

Effects on Fetal Rat Organogenesis:

Approximately ⅓ of the fetal rats were removed per litter, fixed with Bouins solution and then manually sectioned, with the various internal organs being then observed under the dissecting microscope. The results indicated that, of the 17 fetal rats examined in the aspirin positive group, 2 were hydrocephalic. But there was no abnormality in the development of the brain, jaw, tongue, lips, eyes, spinal cord, heart, lungs, kidneys, livers, bladder, and genitals found in the fetal rats examined from the negative control group (40 counts), the low dose group (39 counts), the medium dose group (53 counts), and the high dose group (56 counts).

These results indicate that none of the tested dosages of the GASP had any noticeable effects on indexes, such as the weight gain of the pregnant rats, early embryo geneses, fetal growth and development, and the skeletal development and development of the internal organs of the fetal rats. It was therefore concluded that, in accordance with the procedure for toxicological testing in the "Guide to Researches on Traditional Chinese Medicines and New Drugs," under the present test conditions, the GASP has no teratogenic effects on rats.

administration the animals were sacrificed by dislocation of the cervical vertebra. The femur was then removed, the muscle stripped away, and the bone marrow flushed out using phosphate buffer, centrifuged, fixed hyponotically and the chromosome sample is prepared using methods routine in the art. It was then stained for 10 min using 10% Giemsa's stain (pH 6.8).

Well dispersed Metaphase cells were selected for observation under the oil immersion lens. One hundred (100) metaphase cells were observed per animal, the number of cells with chromosomal aberrations noted, and the chromosomal aberration rate calculated. The data obtained were analyzed statistically calculated using SPSS for Windows 8.0 (t-test).

A comparison of the chromosomal aberration rate between the various GASP dosage groups (using the GASP capsules) and the negative control group showed that the difference was not significant ($p>0.05$), while the chromosomal aberration rate of the CP group was noticeably higher than that of the negative control group ($p<0.01$).

(Results Shown in Table 8).

TABLE 8

Effects of the *Ganoderma lucidum* Spore Powder Activated by Germination on the Chromosomal Aberration Rate in the Bone Marrow Cells of Mice

| Group | GASP Dosage (mg/kg) | No. animals | No. cells counted | No. aberrant cells | Type and Number of Aberration | Chromosomal Aberration Rate (%) |
|---|---|---|---|---|---|---|
| GASP | 10000 | 5 | 500 | 3 | b(4) | 0.6 |
| GASP | 2000 | 5 | 500 | 4 | b(4) | 0.8 |
| GASP | 400 | 5 | 500 | 3 | b(3) | 0.6 |
| Negative control | | 5 | 500 | 3 | b(3) | 0.6 |
| Positive control | | 5 | 500 | 115 | b(48) I(35) f(59) | 25.0* | b: indicating chromosomal breakage.
I: indicating chromosomal fragmentation.
f: indicating chromosal fusion.
*$p < 0.01$.

EXAMPLE 3

In order to investigate whether GASP increased the chromosomal aberration rate, its effects were tested on bone marrow cells of mice.

Male NIH mice weighing 22–25 g, provided by the Guangdong Provincial Animal Center for Medical Experiments, were used. Dosages used were based on the fifty percent lethal dose ($LD_{50}$) for mice, which is greater than 21.5 g/kg (data provided by Medical College of Jinan University). In the present test ½ the $LD_{50}$, ⅒ the $LD_{50}$, and 1/50 $LD_{50}$ were selected as the experimental dosages, i.e. 10000 mg/kg, 2000 mg/kg, and 400 mg/kg. A negative control group and a positive control group (40 mg/kg cyclophosphamide) were also used. Each group contained 5 mice. Dosages were administered once a day for 3 consecutive days, orally via gavage.

GASP was weighed out, an appropriate amount of distilled water added and ground in a mortar. Distilled water was then added to adjust the suspension to the required concentration. The compound was orally administered through gavage at 0.4 ml/10 g of body weight. The negative control group was given an equivalent amount of distilled water, while the positive control group was given cyclophosphamide ("CP") orally through gavage at 40 mg/kg (single administration). Twenty four (24) hours after the last The above results demonstrate that when the GASP was administered at the highest dosage (10000 mg/kg), it did not cause an increase in the chromosomal aberration rate of the bone marrow cells of mice. This in turn confirmed that GASP did not cause an increase in mutation rate when administered at high dosages.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for reducing chromosomal aberration in a mammal, said method comprising administering to a mammal an effective protective amount of germination activated *Ganoderma lucidum* spore powder (GASP) prior to the mammal coming into contact with cyclophosphamide; wherein said chromosomal aberration is caused by exposure to cyclophosphamide.

2. The method of claim 1 wherein said mammal is a human.

3. The method of claim 2 wherein said effective protective amount is between 0.5 and 50 g per day.

4. The method of claim 3 wherein said effective protective amount is between 1 and 25 g per day.

5. A method for reducing chromosomal aberration in a mammal, said method comprising administering to a mammal an effective amount of germination activated *Ganoderma lucidum* spore powder (GASP); wherein said chromosomal aberration is caused by exposure to a toxic substance, wherein said mammal is a pregnant female mammal, and wherein said toxic substance is cyclophosphamide.

6. The method of claim 5, wherein said effective protective amount is between 0.5 and 50 g per day.

7. The method of claim 6, wherein said effective protective amount is between 1 and 25 g per day.

* * * * *